United States Patent [19]

Shields

[11] 4,062,816
[45] Dec. 13, 1977

[54] D-ALA⁵-SOMATOSTATIN AND INTERMEDIATES THERETO

[75] Inventor: James E. Shields, Indianapolis, Ind.

[73] Assignee: Eli Lilly and Company, Indianapolis, Ind.

[21] Appl. No.: 665,979

[22] Filed: Mar. 11, 1976

[51] Int. Cl.² .............................................. C08L 37/00
[52] U.S. Cl. .................................. 260/8; 260/112.5 S
[58] Field of Search .......................... 260/112.5 S, 6, 8

[56] References Cited

U.S. PATENT DOCUMENTS 3,933,784  1/1976  Sarantatis ...................... 260/112.5 S

OTHER PUBLICATIONS

R. Walter et al., Peptides: Chemistry, Structure and Biology, pp. 863-870 (1975).

Primary Examiner—Delbert R. Phillips
Attorney, Agent, or Firm—William C. Martens, Jr.; Everet F. Smith

[57] ABSTRACT

The tetradecapeptide

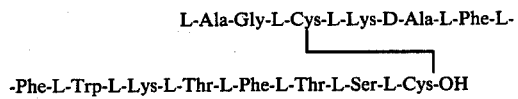

is described along with corresponding non-toxic pharmaceutically-acceptable acid addition salts as well as intermediates useful in the synthesis of the tetradecapeptide. This tetradecapeptide as well as its pharmaceutically acceptable acid addition salts inhibit the secretion of gastric acid.

9 Claims, No Drawings

D-ALA⁵-SOMATOSTATIN AND INTERMEDIATES THERETO

BACKGROUND AND SUMMARY OF THE INVENTION

This invention is directed to the tetradecapeptide

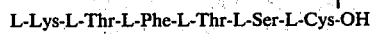

as well as to its pharmaceutically acceptable acid addition salts and to intermediates produced during the synthesis of the tetradecapeptide.

Somatostatin (also known as somatotropin release inhibiting factor) is a tetradecapeptide of the formula

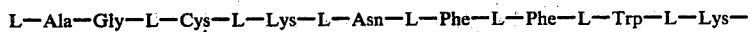
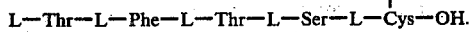

This tetradecapeptide was isolated from ovine hypothalamic extracts and was found to be active in inhibiting the secretion of growth hormone (GH), also known as somatotropin. In this regard, see P. Brazeau, W. Vale, R. Burgus, N. Ling, M. Butcher, J. Rivier, and R. Guillemin, Science, 179, 77 (1973).

The novel tetradecapeptide of this invention has the formula defined above and includes the non-toxic acid addition salts thereof. Its structure differs from that of somatostatin by the presence of a D-alanine residue in position 5 in place of an L-asparagine residue. For convenience sake, the tetradecapeptide of this invention can be referred to as D-Ala⁵-somatostatin.

Thus, this invention is directed to a compound selected from those of the formula

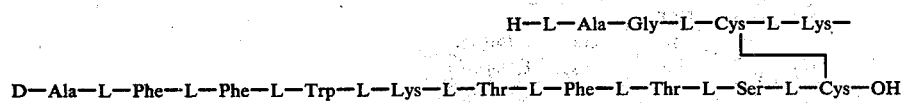

and its pharmaceutically acceptable non-toxic acid addition salts, and R-L-Ala-Gly-L-Cys($R_1$)-L-Lys($R_2$)-D-Ala-L-Phe-L-Phe-L-Trp($R_5$)-L-Lys($R_2$)-L-Thr($R_3$)-L-Phe-L-Thr($R_3$)-L-Ser($R_4$)-L-Cys($R_1$)-X; in which R is hydrogen or an α-amino protecting group;
$R_1$ is hydrogen or a thio protecting group;
$R_2$ is hydrogen or an ε-amino protecting group;
$R_3$ and $R_4$ each are hydrogen or a hydroxy protecting group;
$R_5$ is hydrogen or formyl; and
X is hydroxy or

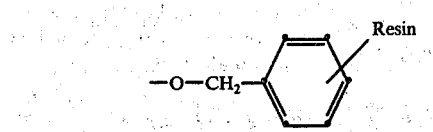

in which the resin is polystyrene; with the proviso that, when X is hydroxy, R, $R_1$, $R_2$, $R_3$, $R_4$, and $R_5$ each are hydrogen; and, when X is

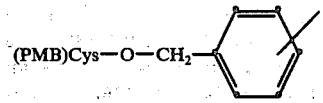

R, $R_1$, $R_2$, $R_3$, and $R_4$ each are other than hydrogen.

DETAILED DESCRIPTION OF THE INVENTION

As indicated above, this invention in part is directed to a compound conveniently referred to as D-Ala⁵-somatostatin as well as to pharmaceutically acceptable non-toxic acid addition salts thereof.

Pharmaceutically acceptable non-toxic acid addition salts include the organic and inorganic acid addition salts, for example, those prepared from acids such as hydrochloric, sulfuric, sulfonic, tartaric, fumaric, hydrobromic, glycolic, citric, maleic, phosphoric, succinic, acetic, nitric, benzoic, ascorbic, p-toluenesulfonic, benzenesulfonic, naphthalenesulfonic, propionic, and the like. Preferably, the acid addition salt is that prepared from acetic acid. Any of the above salts are prepared by conventional methods.

Also contemplated as being within the scope of this invention are intermediates of the formula R-L-Ala-Gly-L-Cys($R_1$)-L-Lys($R_2$)-D-Ala-L-Phe-L-Phe-L-Trp($R_5$)-L-Lys($R_2$)-L-Thr($R_3$)-L-Phe-L-Thr($R_3$)-L-Ser($R_4$)-L-Cys($R_1$)-X. Preferred intermediates include the following:

H-L-Ala-Gly-L-Cys-L-Lys-D-Ala-L-Phe-L-Trp-L-Lys-L-Thr-L-Phe-L-Thr-L-Ser-L-Cys-OH;

and

N-(BOC)-L-Ala-Gly-L-(PMB)Cys-L-(CPOC)Lys-D-Ala-L-Phe-L-Phe-L-(For)Trp-L-(CPOC)Lys-L-(Bzl)Thr-L-Phe-L-(Bzl)Thr-L-(Bzl)Ser-L-

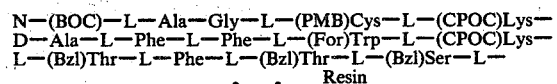

In the above formula defining the intermediates R is either hydrogen or an α-amino protecting group. The α-amino protecting groups contemplated for R are well recognized by those of ordinary skill in the peptide art. Many of these are detailed in the treatise Protective Groups in Organic Chemistry, J. F. W. McOmie, Editor, Plenum Press, New York, 1973, in Chapter 2, authored by J. W. Barton. Illustrative of such protecting groups are benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-methoxybenzyloxycarbonyl, p-nitrobenzyloxycarbonyl, t-butyloxycarbonyl (BOC), t-amyloxycarbonyl, 2-(p-biphenylyl)isopropyloxycarbonyl (BpOC), adamantyloxycarbonyl, isopropyloxycarbonyl, cyclopentyloxycarbonyl, cyclohexyloxycarbonyl, cycloheptyloxycarbonyl, triphenylmethyl (trityl), p-toluenesulfonyl, and the like. Preferably, the α-amino protecting group defined by R is t-butyloxycarbonyl.

$R_1$ represents either the hydrogen of the sulfhydryl group of the cysteine or a protecting group for the sulfhydryl substituent. Illustrative suitable such protecting groups are p-methoxybenzyl, benzyl, benzhydryl, acetamidomethyl, trityl, p-nitrobenzyl, t-butyl, isobutyloxymethyl, as well as any of a number of trityl derivatives. For additional groups, see, for example, Houben-Weyl, *Methodes der Organischen Chemie*, "Synthese von Peptiden", Vols. 15/1 and 15/2, (1974), Stuttgart, Germany. Preferably, the sulfhydryl protecting group defined by $R_1$ is p-methoxybenzyl.

$R_2$ represents either hydrogen on the ε-amino function of the lysine residue or a suitable ε-amino protecting group. Illustrative such groups are the bulk of those mentioned hereinabove as being suitable for use as an ε-amino protecting group. Included as typical such groups are benzyloxycarbonyl, t-butyloxycarbonyl, t-amyloxycarbonyl, cyclopentyloxycarbonyl, adamantyloxycarbonyl, p-methoxybenzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl, isopropyloxycarbonyl, cyclohexyloxycarbonyl, cycloheptyloxycarbonyl, p-toluenesulfonyl, and the like.

As will become apparent hereinafter, the method of preparation of the tetradecapeptide of this invention involves periodic cleavage of the α-amino protecting group from the terminal amino acid present on the peptide chain. Thus, the only limitation with respect to the identity of the ε-amino protecting group on the lysine residue is that it be such that it will not be cleaved under the conditions employed in selectively cleaving the α-amino protecting group. Appropriate selection of the α-amino and the ε-amino protecting groups is a matter well within the knowledge of a peptide chemist of ordinary skill in the art and depends upon the relative ease with which a particular protecting group can be cleaved. Thus, groups such as 2-(p-biphenylyl)isopropyloxycarbonyl (BpOC) and trityl are very labile and can be cleaved even in the presence of mild acid. A moderately strong acid, such as hydrochloric acid, trifluoroacetic acid, or boron trifluoride in acetic acid, is required to cleave other groups such as t-butyloxycarbonyl, t-amyloxycarbonyl, adamantyloxycarbonyl, and p-methoxybenzyloxycarbonyl. Even stronger acid conditions are required to effect cleavage of other protecting groups such as benzyloxycarbonyl, halobenzyloxycarbonyl, p-nitrobenzyloxycarbonyl, cycloalkyloxycarbonyl, and isopropyloxycarbonyl. Cleavage of these latter groups requires drastic acid conditions such as the use of hydrogen bromide, hydrogen fluoride, or boron trifluoroacetate in trifluoroacetic acid. Of course, any of the more labile groups will also be cleaved under the stronger acid conditions. Appropriate selection of the amino protecting groups thus will include the use of a group at the α-amino function which is more labile than that employed as the ε-amino protecting group coupled with cleavage conditions designed to selectively remove only the α-amino function. In this context, $R_2$ preferably is cyclopentyloxycarbonyl, and, in conjunction therewith, the α-amino protecting group of choice for use in each of the amino acids which are added to the peptide chain preferably is t-butyloxycarbonyl.

The groups $R_3$ and $R_4$ both represent hydrogen or, separately, a protecting group for the alcoholic hydroxyl of threonine and serine, respectively. Typical such protecting groups are, for example, $C_1$–$C_4$ alkyl, such as methyl, ethyl, t-butyl, and the like; benzyl; substituted benzyl, such as p-methoxybenzyl, p-nitrobenzyl, p-chlorobenzyl, and the like; $C_1$–$C_3$ alkanoyl, such as formyl, acetyl, and propionyl; triphenylmethyl (trityl); and the like. Preferably, when $R_3$ and $R_4$ are protecting groups, the protecting group of choice in both instances is benzyl.

The group $R_5$ represents either hydrogen or formyl, the latter being a protecting group for the NH of the tryptophan residue. The use of such a protecting group is optional and therefore $R_5$ properly can be hydrogen (N-unprotected) or formyl (N-protected).

The group X represents the carboxyl terminal of the tetradecapeptide chain and can be hydroxyl in which case a free carboxyl group thereby is defined. In addition, X represents the solid resin support to which the carboxyl terminal moiety of the peptide is linked during its synthesis. This solid resin can be represented by the formula

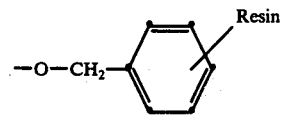

In any of the above, when X represents hydroxyl, R, $R_1$, $R_2$, $R_3$, $R_4$, and $R_5$ each are hydrogen. When X represents the solid resin support, R, $R_1$, $R_2$, $R_3$, and $R_4$ each represent a protecting group.

The following abbreviations, most of which are well known and commonly used in the art, are employed herein:

Ala — Alanine
Cys — Cysteine
Gly — Glycine
Lys — Lysine
Phe — Phenylalanine
Ser — Serine
Thr — Threonine
Trp — Tryptophan
DCC — N,N'-Dicyclohexylcarbodiimide
DMF — N,N-Dimethylformamide
BOC — t-Butyloxycarbonyl
PMB — p-Methoxybenzyl
CPOC — Cyclopentyloxycarbonyl
For — Formyl
Bzl — Benzyl
BpOC — 2-(p-biphenylyl)isopropyloxycarbonyl Although the selection of the particular protecting groups to be employed in preparing the compounds of this invention remains a matter well within the ordinary skill of a peptide chemist, it is well to recognize that the proper selection of the protecting groups is dependent upon the particular succeeding reactions which must be carried out. Thus, the protecting group of choice must be one which is stable both to the reagents and under the conditions employed in the succeeding steps of the reaction sequence. For example, as already discussed to some degree hereinabove, the particular protecting group which is employed must be one which remains intact under the conditions which are employed for cleaving the α-amino protecting group of the terminal amino acid residue of the peptide fragment in preparation for the coupling of the next succeeding amino acid fragment to the peptide chain. It is also important to select, as protecting group, one which will remain intact during the building of the peptide chain and which will be readily removable upon completion of the synthesis of the desired tetradecapeptide product. All of these matters are well within the knowledge and understanding of a peptide chemist of ordinary skill in the art.

As is evident from the above discussion, the tetradecapeptide of this invention can be prepared by solid phase synthesis. This synthesis involves a sequential building of the peptide chain beginning at the C-terminal end of the peptide. Specifically, cysteine first is linked at its C-terminal to the resin by reaction of an amino-protected, S-protected cysteine with a chloromethylated resin or a hydroxymethyl resin. Preparation of a hydroxymethyl resin is described by Bodanszky et al., *Chem. Ind.* (London), 38 1597-98 (1966). The chloromethylated resin is commercially available from Lab Systems, Inc., San Mateo, Calif.

In accomplishing linkage of the carboxyl of the cysteine to the resin, the protected cysteine first is converted to its cesium salt. This salt then is reacted with the resin in accordance with the method described by B. F. Gisin, *Helv. Chim. Acta,* 56, 1476 (1973). Alternatively, the cysteine can be linked to the resin by activation of the carboxyl function of the cysteine molecule by application of readily recognized techniques. For example, the cysteine can be reacted with the resin in the presence of a carboxyl group activating compound such as N,N'-dicyclohexylcarbodiimide (DCC).

Once the C-terminal cysteine has been appropriately linked to the resin support, the remainder of the peptide building sequence involves the step-wise addition of each amino acid to the N-terminal portion of the peptide chain. Necessarily, therefore, the particular sequence which is involved comprises a cleavage of the α-amino protecting group from the amino acid which represents the N-terminal portion of the peptide fragment followed by coupling of the next succeeding amino acid residue to the now free and reactive N-terminal amino acid. Cleavage of the α-amino protecting group can be effected in the presence of an acid such as hydrobromic acid, hydrochloric acid, trifluoroacetic acid, p-toluenesulfonic acid, benzenesulfonic acid, naphthalenesulfonic acid, acetic acid, and the like, with formation of the respective acid addition salt product. Another method which is available for accomplishing cleavage of the amino protecting group involves the use of boron trifluoride. For example, boron trifluoride diethyl etherate in glacial acetic acid will convert the amino-protected peptide fragment to a $BF_3$ complex which then can be converted to the deblocked peptide fragment by treatment with a base such as aqueous potassium bicarbonate. Any of these methods can be employed as long as it is recognized that the method of choice must be one which accomplishes cleavage of the N-terminal α-amino protecting group without disruption of any other protecting groups present on the peptide chain. In this regard, it is preferred that the cleavage of the N-terminal protecting group be accomplished using trifluoroacetic acid. Generally, the cleavage will be carried out at a temperature from about 0° C. to about room temperature.

Once the N-terminal cleavage has been effected, the product which results normally will be in the form of the acid addition salt of the acid which has been employed to accomplish the cleavage of the protecting group. The product then can be converted to the free terminal amino compound by treatment with a mild base, typically a tertiary amine such as pyridine, triethylamine, or the like.

The peptide chain then is ready for reaction with the next succeeding amino acid. This can be accomplished by employing any of several recognized techniques. In order to achieve coupling of the next-succeeding amino acid to the N-terminal peptide chain, an amino acid which has a free carboxyl but which is suitably protected at the α-amino function as well as at any other active moiety is employed. The amino acid then is subjected to conditions which will render the carboxyl function active to the coupling reaction. One such activation technique which can be employed in the synthesis involves the conversion of the amino acid to a mixed anhydride. Thereby, the free carboxyl function of the amino acid is activated by reaction with another acid, typically a carbonic acid in the form of its acid chloride. Examples of such acid chlorides which can be used to form the appropriate mixed anhydrides are ethyl chloroformate, phenyl chloroformate, sec-butyl chloroformate, isobutyl chloroformate, pivaloyl chloride, and the like.

Another method of activating the carboxyl function of the amino acid to achieve coupling is by conversion of the amino acid to its active ester derivative. Examples of such active esters are, for example, a 2,4,5-trichlorophenyl ester, a pentachlorophenyl ester, a p-nitrophenyl ester, an ester formed from 1-hydroxybenzotriazole, and an ester formed from N-hydroxysuccinimide. Another method for effecting coupling of the C-terminal amino acid to the peptide fragment involves carrying out the coupling reaction in the presence of at least an equimolar quantity of N,N'-dicyclohexylcarbodiimide (DCC). This latter method is preferred for preparing the tetradecapeptide of this invention.

Once the desired amino acid sequence has been prepared, the resulting peptide can be removed from the resin support. This is accomplished by treatment of the protected resin-supported tetradecapeptide with hydrogen fluoride. Treatment with hydrogen fluoride cleaves the peptide from the resin; in addition, however, it cleaves all remaining protecting groups present on the reactive moieties located on the peptide chain as well as the α-amino protecting group present at N-terminal amino acid. When hydrogen fluoride is employed to effect the cleavage of the peptide from the resin as well as removal of the protecting groups, it is preferred that the reaction be carried out in the presence of anisole. The presence of anisole has been found to inhibit the potential alkylation of certain amino acid residues present in the peptide chain. In addition, it is preferred that the cleavage be carried out in the presence of ethyl mercaptan. The ethyl mercaptan serves to protect the indole ring of the tryptophan residue and, furthermore, facilitates conversion of the blocked cysteines to their thiol forms. Also, when $R_5$ is formyl, the presence of ethyl mercaptan facilitates hydrogen fluoride cleavage of the formyl group.

Once the cleavage reaction has been accomplished, the product which is obtained is a straight-chain peptide containing 14 amino acid residues. In order to obtain the final product of this invention, it is necessary to treat the straight-chain tetradecapeptide under conditions which will effect its oxidation by converting the two sulfhydryl groups present in the molecule, one at each cysteinyl moiety, to a disulfide bridge. This can be accomplished by treating a dilute solution of the linear tetradecapeptide with any of a variety of oxidizing agents including, for example, iodine, potassium ferricyanide, and the like. Air also can be employed as oxidizing agent, the pH of the mixture generally being from about 2.5 to about 9.0, and preferably from about 7.0 to about 7.6. The concentration of the solution which is employed generally is not greater than about 0.4 mg. of the peptide per milliliter of solution, and usually is about 50 μg./ml.

The compounds of this invention having the disulfide linkage may be administered to warm-blooded mammals, including humans, by any of several methods, including orally, sublingually, subcutaneously, intramuscularly, intravenously, and the like. These compounds are useful in inhibiting the secretion of gastric acid. This inhibitory effect is beneficial in those instances in which the host being treated requires therapeutic treatment of, for example, a gastric ulcer condition. Preferably, the dose range for sublingual or oral administration is about 1 mg. to about 100 mg./kg. of body weight per day. Generally, the dose range for intravenous, subcutaneous, or intramuscular administration is from about 10 μg. to about 1 mg./kg. of body weight per day, and, preferably, is from about 50 μg. to about 100 μg./kg. of body weight per day. It is evident that the dose range will vary widely dependent upon the particular condition which is being treated as well as the severity of the condition.

It is also possible to administer the compounds of this invention in the form of tablets containing other inocuous ingredients. Inert diluents or carriers, for example, magnesium carbonate or lactose, can be used together with conventional disintegrating agents, for example, maize starch and alginic acid, and lubricating agents, for example, magnesium stearate. Typically, the amount of carrier or diluent will range from about 5 to about 95 percent of the final composition, and preferably from about 50 to about 85 percent of the final composition. Suitable flavoring agents also can be employed in the final preparation rendering the composition more palatable for administration.

When the compounds of this invention are to be administered intravenously, suitable carriers may be employed, such as, for example, isotonic saline, phosphate buffer solutions, and the like.

The following examples are illustrative of the preparation of compounds of this invention.

EXAMPLE 1

N-t-BUTYLOXYCARBONYL-L-CYSTEINYL(S-p-METHOXYBENZYL) METHYLATED POLYSTYRENE RESIN

To 50.0 g. of chloromethylated polystyrene resin (Lab Systems, Inc., 0.75 mmoles of chlorine/gram) suspended in 350 ml. of N,N-dimethylformamide (DMF) were added 6.53 grams (12.5 mmoles) of the cesium salt of N-t-butyloxycarbonyl-(S-p-methoxybenzyl)cysteine. The mixture was stirred at 50° C. overnight and was allowed to stand at room temperature for 3 days. The resin then was filtered and washed successively with DMF, a mixture of 90 percent DMF and 10 percent water, DMF, 95% ethanol, methylene chloride, and 95% ethanol. The resin was dried in vacuo at 40° C. and then was suspended in 350 ml. of DMF. Cesium acetate (7.2g.; 37.5 mmoles) was added. The mixture was stirred overnight at 50° C., and then was filtered and was washed successively with DMF, a mixture of 90 percent DMF and 10 percent water, 95% ethanol, methylene chloride, and 95 percent ethanol. The resin then was dried in vacuo at 40° C. to obtain the title compound.

EXAMPLE 2 t-BUTYLOXYCARBONYL-L-ALANYL-GLYCYL-L-(S-p-METHOXYBENZYL)CYSTEINYL-L-(CYCLOPENTYLOXYCARBONYL)-LYSYL-D-ALANYL-L-PHENYLALANYL-L-PHENYLALANYL-L-(FORMYL)TRYPTOPHYL-L-(N-CYCLOPENTYLOXYCARBONYL)LYSYL-L-(O-BENZYL)-THREONYL-L-PHENYLALANYL-L-(O-BENZYL)-THREONYL-L-(O BENZYL)SERYL-L-(S-p-METHOXY-BENZYL)-CYSTEINYL METHYLATED POLYSTYRENE RESIN

To the reaction vessel of a Beckman 990 automatic peptide synthesizer were added 10.0 grams of the product for Example 1. Sequences of deprotection, neutralization, coupling, and a recoupling were carried out for the addition of each amino acid to the peptide. Upon completion of the introduction of the first six amino acids to the cysteine-resin, the resulting heptapeptide resin (11.76 grams) was divided into two portions, and one-half (5.88 grams) was used for introduction of the succeeding seven amino acid moieties. The amino acids which were employed as well as the sequence of their employment is as follows: (1)N-t-butyloxycarbonyl-(O-benzyl)-L-serine; (2) N-t-butyloxy carbonyl-(O-benzyl)-L-threonine; (3) N-t-butyloxycarbonyl-L-phenylalanine; (4) N-t-butyloxycarbonyl-(O-benzyl)-L-threonine; (5) $N^\alpha$-t-butyloxycarbonyl-$N^\epsilon$-cyclopentyloxycarbonyl-L-lysine; (6) $N^\alpha$-t-butyloxycarbonyl-N-formyl-L-tryptophan; (7) N-t-butyloxycarbonyl-L-phenylalanine; (8) N-t-butyloxycarbonyl-L-phenylalanine; (9) N-t-butyloxycarbonyl-D-alanine; (10) $N^\alpha$-t-butyloxycarbonyl-$N^\epsilon$-cyclopentyloxycarbonyl-L-lysine; (11) N-t-butyloxycarbonyl-(S-p-methoxybenzyl)-L-cysteine; (12) N-t-butyloxycarbonylglycine; and (13) N-t-butyloxycarbonyl-L-alanine. The sequence of deprotection, neutralization, coupling, and recoupling for the introduction of each amino acid into the peptide is as follows: (1) three washes (7.0–10.0 ml./gram resin) of 3 minutes each with chloroform; (2) removal of BOC group by treatment twice for 20 minutes each with 7.0–10.0 ml./gram resin of a mixture of 30 percent trifluoroacetic acid, 65 percent chloroform, and 5 percent triethylsilane; (3) two washes (7.0–10.0 ml./gram resin) of 3 minutes each with chloroform; (4) one wash (7.0–10.0 ml./gram resin) of 3 minutes with methylene chloride; (5) three washes (7.0–10.0 ml./gram resin) of 3 minutes each with a mixture of 90 percent t-butyl alcohol and 10 percent t-amyl alcohol; (6) three washes (7.0–10.0 ml./gram resin) of 3 minutes each with methylene chloride; (7) neutralization by three treatments of 3 minutes each with 7.0–10.0 ml./gram resin of 3 percent triethylamine in methylene chloride; (8) three washes (7.0–10.0 ml./gram resin) of 3 minutes each with methylene chloride; (9) three washes (7.0–10.0 ml. /gram resin) of 3 minutes each with a mixture of 90 percent t-butyl alcohol and 10 percent t-amyl alcohol; (10) three washes (7.0–10.0 ml./gram resin) of 3 minutes each with methylene chloride; (11) addition of 1.0 mmole/gram resin of the protected amino acid and 1.0 mmole/gram resin of N,N'-dicyclohexylcarbodiimide (DCC) in 7.0–10.0 ml./gram resin of methylene chloride followed by mixing for 120 minutes; (12) three washes (7.0–10.0 ml./gram resin) of 3 minutes each with methylene chloride; (13) three washes (7.0–10.0 ml./gram resin) of 3 minutes each with a mixture of 90 percent t-butyl alcohol and 10 percent t-amyl alcohol; (14) three washes (7.0–10.0 ml./gram resin) of 3 minutes each with methylene chloride; (15) neutralization by three treatments of 3 minutes each with 7.0–10.0 ml./gram resin of 3 percent triethylamine in methylene chloride; (16) three washes (7.0–10.0 ml./gram resin) of 3 minutes each with methylene chloride; (17) three washes (7.0–10.0 ml./gram resin) of 3 minutes each with a mixture of 90 percent t-butyl alcohol and 10 percent t-amyl alcohol; (18) three washes (7.0–10.0 ml./gram resin) of three minutes each with methylene chloride; (19) three washes (7.0–10.0 ml./gram resin) of 3 minutes each with DMF; (20) addition of 1.0 mmole/gram resin of the protected amino acid and 1.0 mmole/gram resin of N,N'-dicyclohexylcarbodiimide (DCC) in 7.0–10.0 ml./gram resin of a 1:1 mixture of DMF and methylene chloride followed by mixing for 120 minutes; (21) three washes (7.0–10.0 ml./gram resin) of 3 minutes each with DMF; (22) three washes (7.0–10.0 ml./gram resin) of 3 minutes each with methylene chloride; (23) three washes (7.0–10.0 ml./gram resin) of three minutes each with a mixture of 90 percent t-butyl alcohol and 10 percent t-amyl alcohol; (24) three washes (7.0–10.0 mg./gram resin) of 3 minutes each with methylene chloride; (25) neutralization by three treatments of 3 minutes each with 7.0–10.0 ml./gram resin of 3 percent triethylamine in methylene chloride; (26) three washes (7.0–10.0 mg./gram resin) of 3 minutes each with methylene chloride; (27) three washes (7.0–10.0 ml./gram resin) of 3 minutes each with a mixture of 90 percent t-butyl alcohol and 10 percent t-amyl alcohol; and (28) three washes (7.0–10.0 mg./gram resin) of 3 minutes each with methylene chloride.

The finished peptide-resin was dried in vacuo at 40° C. A sample of the product then was hydrolyzed by refluxing it for 21 hours in a mixture of hydrochloric acid and dioxane. Amino acid analysis of the resulting product gave the following results, lysine being employed as standard: Thr, 2.12; Ser, 0.94; Gly, 1.23; Ala, 2.74; Phe, 2.76; Lys, 2.00; Trp, 0.72. The presence of cysteine was not determined since it is destroyed by the method of analysis.

EXAMPLE 3

L-ALANYL-GLYCYL-L-CYSTEINYL-L-LYSYL-D-ALANYL-L-PHENYLALANYL-L-PHENYL-ALANYL-L-TRYPTOPHYL-L-LYSYL-L-THREONYL-L-PHENYLALANYL-L-THREONYL-L-SERYL-L-CYSTEINE

To a mixture of 10 ml. of anisole and 10 ml. of ethyl mercaptan were added 3.42 grams of the protected tetradecapeptide-resin of Example 2. The mixture was cooled in liquid nitrogen, and 37 ml. of liquid hydrogen fluoride were added by distillation. The resulting mixture was allowed to warm to 0° C. and was stirred for 1.5 hours. The hydrogen fluoride then was distilled off, and ether was added to the remaining mixture. The resulting solid material was collected by filtration and washed with ether. The product was dried, and the deprotected tetradecapeptide was extracted from the resin mixture using 1M acetic acid. The acetic acid solution then was immediately lyophilized to dryness in the dark. The resulting white solid was suspended in a mixture of 15 ml. of 1M acetic acid and 4 ml. of glacial acetic acid. The resulting suspension was filtered, and the filtrate was absorbed on a Sephadex G-25 F column. The chromatographic conditions were: solvent, deoxygenated 1M acetic acid; column size, 7.5 ×150 cm.; temperature, 26° C.; flow rate, 635 ml./hour; fraction volume, 22.2 ml.

Absorbance at 280 m$\mu$ of each fraction plotted versus fraction number indicated three broad, overlapping peaks. The first peak was the largest and was determined by UV spectra to be good product. This product was collected and lyophilized to dryness. The material then was re-chromatographed using the following conditions: solvent, deoxygenated 0.2M acetic acid; column size, 5.0 ×150 cm.; temperature, 26° C.; flow rate, 513 ml./hour; fraction volume, 17.1 ml.

Absorbance at 280 m$\mu$ of each fraction plotted versus fraction number indicated a main peak with a front shoulder and a low, broad peak in front of the main peak. A collection of three sets of fractions was made. The fractions which were combined and their effluent volumes are as follows:

Fractions 76–125: (1283–2138 ml.)
Fractions 126–139: (2139–2377 ml.)
Fractions 140–163: (2378–2789 ml.)

UV spectroscopy indicated that the third sample (411 ml.) was the best product and that it contained 36.4 mg. of the product.

EXAMPLE 4

OXIDATION TO D-ALA$^5$-SOMATOSTATIN

The solution of reduced D-Ala$^5$-somatostatin from Example 3 was shown by UV spectroscopy to contain product in a concentration of 88.2 $\mu$g./ml. The solution was diluted with 316 ml. of distilled water to achieve a 50 $\mu$g./ml. concentration. Concentrated ammonium hydroxide was added to adjust the pH of the mixture to 7.0. The solution was vigorously stirred at room temperature in the dark for 40 hours after which an Ellman titration indicated that oxidation was complete. The mixture was concentrated in vacuo to a volume of about 5 ml., and 5 ml. of 50% acetic acid were added. The resulting solution then was desalted on Sephadex G-25F in 50% acetic acid under the following conditions: solvent, deoxygenated 50% acetic acid; column size, 2.5 ×90 cm.; temperature, 26° C.; flow rate, 96 ml./hour; fraction volume, 4.8 ml.

Absorbance at 280 m$\mu$ of each fraction plotted versus fraction number showed two large peaks. The first peak represented the aggregated forms of the analog, and the second peak represented good, monomeric product. Product represented by the second peak was collected and lyophilized to dryness. The resulting white solid was dissolved in 5 ml. of deoxygenated 0.2 M acetic acid. The solution was absorbed on a Sephadex G-25 F column. The chromatographic conditions were as follows: solvent, deoxygenated 0.2 M acetic acid; column size, 2.5 ×180 cm.; temperature, 26° C.; flow rate, 100 ml./hour; fraction volume, 8.33 ml.

Absorbance at 280 mµ of each fraction plotted versus fraction number indicated one large peak with two shoulders, one on each side, and a low, broad peak preceding it. UV spectroscopy showed the large peak to be good product. Fractions 93-98 were combined (effluent volumes of 766-816 ml.) and lyophilized to dryness to obtain 10.26 mg. of the desired product.

Optical rotation $[\alpha]_D^{26} = -17.5°$ (1 percent acetic acid).

Amino acid analysis: $Ala_{2.28}$ $Gly_{1.14}$ $Cys_{1.84}$ $Lys_{2.0}$ $Phe_{2.88}$ $Trp_{0.88}$ $Thr_{2.10}$ $Ser_{0.76}$.

The product from Example 4 was tested for its activity in inhibiting the release of growth hormone. The procedure which was employed is carried out using mature male Spraque-Dawley rats (Laboratory Supply Company, Indianapolis, Ind.). The test is a modification of the method of P. Brazeau, W. Vale, and R. Guillemen, *Endocrinology*, 94 184 (1974). In this assay, three groups of eight rats each were employed. First, sodium pentobarbital was administered to all forty rats to stimulate growth hormone secretion. One of the groups of eight rats is the control group and received only saline. A second of the groups received somatostatin at 50 µg./rat, subcutaneously. The third group received D-Ala⁵-somatostatin at 50 µg./rat, subcutaneously. The degree of inhibition of serum growth hormone concentration then was determined with respect to the control group, and the relative activities of D-Ala⁵-somatostatin and somatostatin itself were compared. At a dose level of 50 µg./rat, D-Ala⁵-somatostatin inhibited the increase in serum growth hormone concentration by 40-50 percent, while somatostatin itself produced a 90 percent inhibition.

The product from Example 4 also was tested for its activity in inhibiting glucagon and insulin secretion. Normal mongrel dogs of either sex were fasted overnight. Control blood samples were obtained, and then an intravenous infusion of saline, somatostatin, or D-Ala⁵-somatostatin was started. After 30 minutes, L-alanine additionally was administered intravenously for a period of 15 minutes. The infusion of saline, somatostatin, of D-Ala⁵-somatostatin was continued for 15 minutes after completion of the alanine infusion. The total dose of somatostatin or D-Ala⁵-somatostatin which was infused is 200-500 µg/dog (0.20-0.30 µg/kg/ minute), and the total dose of L-alanine infused was 1 mmol.kg./15 minutes.

Somatostatin infusion caused a decrease in basal serum insulin concentration and inhibited the rise in concentration of both glucagon and insulin during the infusion of L-alanine. In comparison, the D-Ala⁵-somatostatin, infused at a rate of 0.230 µg/kg/min., did not affect the increase in serum glucagon concentration normally produced by L-alanine and caused a brief increase in insulin concentration before the alanine infusion was started. In addition, this compound did not inhibit the increase in insulin secretion normally produced by the infusion of L-alanine.

The product from Example 4 was also tested for its activity in inhibiting gastric acid secretion. Large 5-6 inch bullfrogs were pithed. The gastric mucosa was freed from the muscle layers and was bisected longitudinally. The two halves were mounted in separate acrylic plastic chambers. The secretory area which was exposed was 2.85 square centimeters, and the volume of each half of the chamber was 5 ml. The solutions which were used to bathe the mucosa were the same as those used by Durbin et al., *Biochemica et Biophysics Acta*, 321, 553-560 (1973), with the exception that the serosal fluid contained sodium dihydrogen phosphate at a 1 millimolar concentration. Both sides of the chamber were aerated with a mixture of 95% oxygen and 5% carbon dioxide. The acid secretory rate was followed by maintaining the secretory solution at a pH of 4.5.

A concentration of $1 \times 10^{-5}$ moles per liter of pentagastrin was used on the serosal side of the tissue to stimulate the acid secretory response. The serosal fluid was renewed every 40 minutes to prevent lowering of pentagastrin concentration by enzymatic hydrolysis of the peptide bonds. Addition of the compound to be tested was done by placing it in the serosal fluid each time the bathing solution was changed.

Spontaneous acid outputs for pentagastrin-stimulated secretion producing no less than 8 microequivalents/hour of acid served as controls. The effect of inhibition on gastric acid secretion was expressed as percent of inhibition from the control periods preceding the introduction of the test compound into the serosal buffer. Only one of the halves of the gastric mucosa was treated wth the test compound, the other half serving as control to insure continued viability of the tissue. After establishing steady state secretion, the test compound was added to the nutrient solution in an amount sufficient to attain an inhibitor concentration of $1 \times 10^{-5}$ moles/liter. The acid was continually titrated to pH 4.5, and the volume of 12.5 mM sodium hydroxide utilized each 20 minutes was used to determine the acid secretory rate. The results were expressed as micro equivalents of acid secreted per hour.

Using this method of evaluation, somatostatin itself produced a percent inhibition of gastric acid secretion of 53.37 plus or minus 6.05 whereas D-Ala⁵-somatostatin produced a percent inhibition of gastric acid secretion of 84.05 plus or minus 5.47.

I claim:
1. A compound of the formula

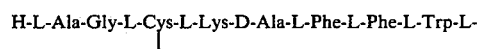

and its pharmaceutically acceptable non-toxic acid addition salts, and intermediates to said compound, said intermediates having the formula R-L-Ala-Gly-L-Cys(R₁)-L-Lys(R₂)-D-Ala-L-Phe-L-Phe-L-Trp(R₅)-L-Lys(R₂)-L-Thr(R₃)-L-Phe-L-Thr(R₃)-L-Ser(R₄)-L-Cys(R₁)-X; in which R is hydrogen or an α-amino protecting group;
R₁ is hydrogen or a thio protecting group;
R₂ is hydrogen or an ε-amino protecting group;
R₃ and R₄ each are hydrogen or a hydroxy protecting group;
R₅ is hydrogen or formyl; and
X is hydroxy or

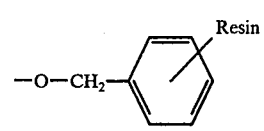

in which the resin is polystyrene; with the proviso that, when X is hydroxy, R, R₁, R₂, R₃, R₄, and R₅ each are hydrogen, and, when X is

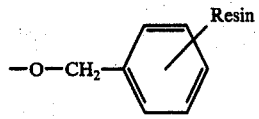

R, $R_1$, $R_2$, $R_3$, and $R_4$ each are other than hydrogen.

2. Compound of claim 1, having the formula

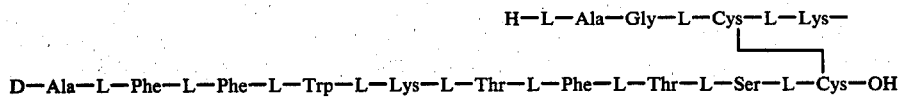

and pharmaceutically acceptable non-toxic acid addition salts thereof.

3. Compound of claim 1, having the formula R-L-Ala-Gly-L-Cys($R_1$)-L-Lys($R_2$)-D-Ala-L-Phe-L-Phe-L-Trp($R_5$)-L-Lys($R_2$)-L-Thr($R_3$)-L-Phe-L-Thr-($R_3$)-L-Ser($R_4$)-L-Cys($R_1$)-X.

4. Compound of claim 3, in which X is hydroxy.

5. Compound of claim 3, in which R is t-butyloxycarbonyl.

6. Compound of claim 3, in which $R_1$ is p-methoxybenzyl.

7. Compound of claim 3, in which $R_2$ is cyclopentyloxycarbonyl.

8. Compound of claim 3, in which $R_3$ and $R_4$ are benzyl.

9. Compound of claim 3, having the formula

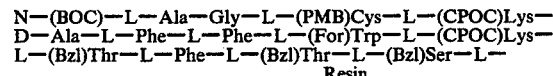
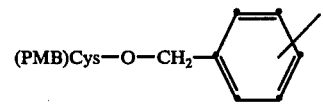

* * * * *